(12) United States Patent
Chang et al.

(10) Patent No.: US 11,684,687 B2
(45) Date of Patent: Jun. 27, 2023

(54) AUTOMATIC FLOOR-DISINFECTION ROBOT FOR HOSPITAL ROOMS

(71) Applicants: SOUTHWEST JIAOTONG UNIVERSITY, Chengdu (CN); LAOKEN MEDICAL TECHNOLOGY CO., LTD, Chengdu (CN)

(72) Inventors: Xianghui Chang, Chengdu (CN); Bowen Ma, Chengdu (CN); Qijun Liu, Chengdu (CN); Xia Liu, Chengdu (CN); Yan Yan, Chengdu (CN); Weidong Qiu, Chengdu (CN); Xihao Jin, Chengdu (CN); Xiang Li, Chengdu (CN); Miao Zhang, Chengdu (CN); Yun Wei, Chengdu (CN)

(73) Assignees: SOUTHWEST JIAOTONG UNIVERSITY, Chengdu (CN); LAOKEN MEDICAL TECHNOLOGY CO., LTD., Chengdu (CN)

( * ) Notice: Subject to any disclaimer, the term of this patent is extended or adjusted under 35 U.S.C. 154(b) by 0 days.

(21) Appl. No.: 18/063,577

(22) Filed: Dec. 8, 2022

(65) Prior Publication Data
US 2023/0111199 A1 Apr. 13, 2023

Related U.S. Application Data

(63) Continuation of application No. PCT/CN2022/102323, filed on Jun. 29, 2022.

(30) Foreign Application Priority Data

Aug. 3, 2021 (CN) .......................... 202110885094.5

(51) Int. Cl.
*A61L 2/24* (2006.01)
*A47L 11/24* (2006.01)
(Continued)

(52) U.S. Cl.
CPC ................. *A61L 2/24* (2013.01); *A47L 11/24* (2013.01); *A47L 11/4002* (2013.01);
(Continued)

(58) Field of Classification Search
CPC ............. A47L 2201/00; A47L 2201/04; A47L 2201/06; A47L 9/009; A47L 9/2826; A47L 11/4011; A47L 11/24
See application file for complete search history.

(56) References Cited

U.S. PATENT DOCUMENTS

2017/0001311 A1* 1/2017 Bushman .............. A47L 9/2852

FOREIGN PATENT DOCUMENTS

| CN | 106352733 A | 1/2017 | |
| CN | 107744370 A * | 3/2018 | ............. A47L 11/24 |

(Continued)

*Primary Examiner* — Joel D Crandall (57) ABSTRACT

An automatic floor-disinfection robot for floors of hospital rooms, including a moving device, a alarm and a disinfection device. The moving device is a disc-shaped robot, and includes a chassis moving mechanism, a support plate and a top plate arranged successively from bottom to top. The disinfection device includes a disinfection assembly and a baffle. The disinfection assembly includes a liquid supply mechanism, a liquid spray mechanism and a fan.

9 Claims, 8 Drawing Sheets

(51) Int. Cl.
*A47L 11/40* (2006.01)
*A61L 2/18* (2006.01)

(52) U.S. Cl.
CPC ....... *A47L 11/4011* (2013.01); *A47L 11/4038* (2013.01); *A47L 11/4066* (2013.01); *A47L 11/4077* (2013.01); *A47L 11/4083* (2013.01); *A47L 11/4088* (2013.01); *A61L 2/18* (2013.01); *A47L 2201/04* (2013.01); *A47L 2201/06* (2013.01); *A61L 2202/14* (2013.01); *A61L 2202/15* (2013.01); *A61L 2202/16* (2013.01); *A61L 2202/17* (2013.01)

(56) References Cited

FOREIGN PATENT DOCUMENTS

| | | | |
|---|---|---|---|
| CN | 108606732 | A | 10/2018 |
| CN | 108656128 | A | 10/2018 |
| CN | 111035314 | A | 4/2020 |
| CN | 111466840 | A | 7/2020 |
| CN | 112190186 | A | 1/2021 |
| CN | 212474826 | U | 2/2021 |
| CN | 212477148 | U | 2/2021 |
| CN | 212698729 | U | 3/2021 |
| CN | 112603201 | A | 4/2021 |
| CN | 212913988 | U | 4/2021 |
| CN | 213113477 | U | 5/2021 |
| CN | 213374020 | U | 6/2021 |
| CN | 113842482 | A | 12/2021 |
| JP | 3722861 | B2 * | 11/2005 |
| WO | 2013191465 | A1 | 12/2013 |
| WO | 2019206335 | A1 | 10/2019 |

* cited by examiner

AUTOMATIC FLOOR-DISINFECTION ROBOT FOR HOSPITAL ROOMS

CROSS-REFERENCE TO RELATED APPLICATIONS

This application is a continuation of International Patent Application No. PCT/CN2022/102323, filed on Jun. 29, 2022, which claims the benefit of priority from Chinese Patent Application No. 202110885094.5, filed on Aug. 3, 2021. The content of the aforementioned applications, including any intervening amendments thereto, is incorporated herein by reference in its entirety.

TECHNICAL FIELD

The present disclosure relates to medical devices, and more particular to an automatic floor-disinfection robot for hospital rooms.

BACKGROUND

The hospital rooms, especially the inpatient wards, are commonly contaminated with various bacteria. In order to satisfy the sterilization and disinfection requirements, it is required to frequently clean and disinfect the passages and floors of the hospital. Usually, a disinfectant is sprayed onto the floor for disinfection.

Chinese Patent Application No. 201911405364.7 disclosed a disinfection robot for floors of hospital rooms, including a disinfectant storage chamber, an external storage mechanism, a lower fixing frame, an upper fixing frame, a connecting frame and a moving mechanism. The moving mechanism is arranged in the lower fixing frame and the upper fixing frame. Four external storage mechanisms are fixedly connected to four edges of the lower fixing frame, respectively. The four external storage mechanisms are all communicated with the disinfectant storage chamber. The upper fixing frame is fixedly connected to the lower fixing frame through four connecting frames. The four connecting frames are fixedly connected to the moving mechanism, a connecting shaft tube, a liquid throw-away mechanism, a liquid spreader and a motor. A base plate is fixedly connected to a bottom surface of the lower fixing frame. The connecting shaft tube is rotatably connected to a lower end of the disinfectant storage chamber. The throw-away mechanism is fixedly connected to a lower end of the connecting shaft tube. Four liquid spreaders are provided, and are rotatably connected to four corners of the base plate, respectively. An upper end of the connecting shaft tube is provided with a first gear. An upper end of each liquid spreader is provided with a second gear. Four second gears are engaged with the first gear for transmission. The motor is fixedly connected to a side wall of the base plate. An output shaft of the motor is fixedly connected to a third gear. The third gear is engaged with one of the four second gears for transmission.

Unfortunately, regarding the above-mentioned structure, the disinfectant will be inevitably sprayed onto obstacles, it is also easy to spray the disinfectant onto the wall at the corner, resulting in unnecessary troubles. Therefore, it is urgently needed to develop an automatic floor-disinfection robot that can prevent the obstacles from being contaminated with the disinfection solution.

SUMMARY

To overcome the above-mentioned defects in the prior art, the present disclosure provides an automatic floor-disinfection robot for hospital rooms, including a moving device, a alarm and a disinfection device. The moving device is a disc-shaped robot, and includes a chassis moving mechanism, a support plate and a top plate arranged successively from bottom to top. The disinfection device includes a disinfection assembly and a baffle. The disinfection assembly includes a liquid supply mechanism, a liquid spray mechanism and a fan. Through the integration of the moving device and the disinfection device, this disclosure realizes the automatic and comprehensive disinfection of floors of hospital rooms. The baffle can protect the obstacles from being contaminated with the disinfectant. By means of the liquid spray mechanism and the fan, the disinfectant can be uniformly sprayed onto the floor to enable the sufficient disinfection.

Technical solutions of the disclosure are described as follows.

Provided herein is an automatic floor-disinfection robot for hospital rooms, comprising:
a moving device; and
a disinfection device;
wherein the disinfection device is arranged on the moving device;
the moving device comprises a chassis moving mechanism, a support plate and a top plate arranged successively from bottom to top; a bottom wall of the chassis moving mechanism is provided with a driving device and a wheel; the wheel is in transmission connection with the driving device; a control panel is arranged on the top plate; a battery, an electric control board and a control system are arranged inside the top plate; and the control system is arranged on the electric control board;
the disinfection device comprises a disinfection assembly and a baffle;
the disinfection assembly comprises a liquid supply mechanism, a liquid spray mechanism and a fan; the liquid supply mechanism is arranged on the moving device; the liquid spray mechanism is arranged below the liquid supply mechanism; and the fan is arranged at a bottom center of the moving device; and
the baffle is configured to prevent the liquid spray mechanism from spraying a disinfectant onto an obstacle; the baffle is arranged on a periphery of the moving device; the baffle has an arc-shaped structure, and is rotatable along the periphery of the moving device; the baffle and the top plate are arranged coaxially; the top plate is connected to the support plate through a support column; the support column is provided with a first boss; a sleeve is pivotally connected to the first boss; the baffle is fixedly connected to the sleeve through a connecting rod; a ring gear is fixedly sleeved on the sleeve; a driving gear is provided at a side of the ring gear, and is engaged with the ring gear; a rotating motor is fixedly arranged inside the top plate; the rotating motor is configured to drive the driving gear to rotate; and the rotating motor is electrically connected to the control system.

In some embodiments, a peripheral side wall of the baffle is provided with a cushion; a bottom of the baffle is provided with a brush; and the brush is in contact with a floor to be disinfected; and
the automatic floor-disinfection robot further comprises an omnidirectional camera and an alarm; the omnidirectional camera and the alarm are arranged above the top plate; and the omnidirectional camera and the alarm are electrically connected to the control system.

In some embodiments, the liquid supply mechanism comprises a liquid storage vessel; a middle part of the liquid storage vessel is provided with a connecting hole; the liquid storage vessel is sleeved on the support column through the connection hole; the liquid storage vessel is also provided with a feeding port; a top of the feeding port penetrates upward a top surface of the top plate; a cover is arranged on the feeding port; a bottom of the liquid storage vessel is provided with at least one discharge port; and the at least one discharge port is communicated with the liquid spray mechanisms.

In some embodiments, the number of the liquid spray mechanism is four; four liquid spray mechanisms are evenly and circumferentially arranged at the chassis moving mechanism; the number of the at least one discharge port is four; four discharge ports are communicated with the four liquid spray mechanisms in one-to-one correspondence; and the chassis moving mechanism is fixedly connected to the support plate through four upright columns.

In some embodiments, each of the four liquid spray mechanisms comprises a spray pipe, a ball bearing, a hose and a solenoid valve; the ball bearing is fixedly sleeved on an outer circumference of the spray pipe; a top end of the spray pipe is connected to the discharge port through the hose; the solenoid valve is arranged at a connection between the discharge port and the hose; the solenoid valve is electrically connected to the control system; and a locking ring is arranged at a connection between the hose and the spray pipe for fixing.

In some embodiments, a bottom end of the spray pipe is provided with a second boss; four sweeping brushes are fixedly connected to the second boss; a brush end of each of the four sweeping brush is in contact with a floor to be disinfected; and the four sweeping brushes are evenly arranged around the fan.

In some embodiments, a circumferential wall of a lower portion of the spray pipe is provided with a plurality of spray ports; the chassis moving mechanism is provided with a frame corresponding to the spray pipe; a driving motor is arranged on the frame; the driving motor is electrically connected to the control system; an output end of the driving motor is connected to an upper portion of the spray pipe through a synchronous belt; and the driving motor is configured to drive the spray pipe to rotate around the ball bearing.

In an embodiment, a covering plate is sleevedly provided on the spray pipe; an umbrella-shaped opening is arranged in the covering plate to cover a lower portion of the spray pipe; and the spray pipe is centrally located below the covering plate.

In some embodiments, the four liquid spray mechanisms consist of a first liquid spray mechanism, a second liquid spray mechanism, a third liquid spray mechanism and a fourth liquid spray mechanism; the first liquid spray mechanism is capable of moving horizontally; a periphery of the chassis moving mechanism is formed by straight edges; the first liquid spray mechanism is arranged on a sliding plate; an edge of the chassis moving mechanism corresponding to the first liquid spray mechanism is provided with a linear actuator; the linear actuator is configured to drive the sliding plate to move horizontally along the edge corresponding to the first liquid spray mechanism; the chassis moving mechanism is further provided with an elongated hole; and the elongated hole does not hinder horizontal motion of the first liquid spray mechanism.

In some embodiments, the linear actuator comprises a rectangular frame and a threaded shaft; the rectangular frame is connected to a side wall of the chassis moving mechanism; the threaded shaft is penetratedly arranged in the rectangular frame; two ends of the threaded shaft are pivotally connected to two side walls of the rectangular frame, respectively; an outer side wall of the rectangular frame is provided with a micro motor; an output shaft of the micro motor is fixedly connected to the threaded shaft; the micro motor is electrically connected to the control system; the micro motor is configured to drive the threaded shaft to rotate; an outer side of the sliding plate is fixedly connected to a thread bushing; the thread bushing is embedded in the rectangular frame; the threaded shaft is penetratedly arranged in the thread bushing, and is threadedly connected with the thread bushing; and the threaded shaft is configured to rotate to drive the sliding plate and the liquid spray mechanism arranged on the sliding plate to move laterally along the elongated hole.

Compared to the prior art, this application has the following beneficial effects.

1. Through the cooperation of the moving device and the disinfection device, the automatic floor-disinfection robot provided herein can sufficiently disinfect the floors of hospital rooms. A baffle is provided to protect the obstacles from being contaminated with the disinfectant. By means of the liquid spray mechanisms and the fan, the disinfectant can be uniformly spread onto the floor.

2. The baffle is provided to prevent the disinfectant from being sprayed onto the obstacles, so as to ensure the cleanness of the obstacles. Consequently, it is ensured that only the floor is sprayed with the disinfectant.

3. Regarding the automatic floor-disinfection robot provided herein, the baffle can rotate along the circumferential direction of the top plate, such that the obstacles at all directions can be protected from being sprayed with the disinfectant.

4. The disinfectant is stored in the liquid storage vessel and fed to the liquid spray mechanism to be sprayed onto the floor, enabling the automatic and efficient disinfection.

5. The solenoid valve is provided to control the liquid supply from the liquid storage vessel, such that the spray amount of the disinfectant from the spray pipe can be controlled, enabling the quantitative and uniform spraying and avoiding the insufficient and excessive spraying.

6. Through the cooperation of the sweeping brush and the fan, after the disinfectant can be further spread by the fan after applied to the floor by the sweeping brush, so as to reach the wide and uniform spraying and enhancing the disinfection effect.

7. By arranging the plurality of spray ports, the sweeping brushes can be sprayed with the disinfectant, leading to a uniform dispersion of the disinfectant on the sweeping brush. In consequence, the sweeping brush can uniformly apply the disinfectant on the floor.

8. By means of the umbrella-shaped opening, the spray ports are shielded, and the disinfectant sprayed from the spray ports will sputter downward. Therefore, the sweeping brush can be sprayed with the disinfectant, and the obstacles will free from splashes of the disinfectant.

9. Due to the sliding plate, the liquid spray mechanism is movable, which makes sure that the corner floor can also be disinfected, avoiding situations such as some floors cannot be applied with the disinfectant by the sweeping brush, and achieving a comprehensive disinfection of floor.

10. Through the integration of the omnidirectional camera and the alarm, the moving device can move according to the surrounding and prevent random movement and failures of avoiding obstacles. Consequently, the moving device can not only disinfect the floor, but also protect people.

In the drawings, 1, moving device; 2, chassis moving mechanism; 3, support plate; 4, top plate; 5, disinfection device; 6, baffle; 7, liquid supply mechanism; 8, liquid spray mechanism; 9, fan; 10, cushion; 11, brush; 12; support column; 13, sleeve; 14, connecting rod; 15, ring gear; 16, driving gear; 17, rotating motor; 18, liquid storage vessel; 19, support base; 20, feeding port; 21, discharge port; 22, upright column; 23, spray pipe; 24, ball bearing; 25, hose; 26, solenoid valve; 27, locking ring; 28, second boss; 29, sweeping brush; 30, spray port; 31, driving motor; 32, synchronous belt; 33, covering plate; 34, sliding plate; 35, linear actuator; 36, elongated hole; 37, omnidirectional camera; and 38, alarm.

DETAILED DESCRIPTION OF EMBODIMENTS

The disclosure will be described in detail below with reference to the embodiments and accompanying drawings to enable those skilled in the art to implement the technical solutions of the disclosure. Obviously, described below are merely some embodiments of this disclosure, and other embodiments may be obtained by those skilled in the art based on the embodiments disclosed herein without paying creative effort.

Provided herein is an automatic floor-disinfection robot for hospital rooms, which can sufficiently and automatically disinfect a floor to be disinfected such as hospital rooms, wards. Referring to FIGS. 1-15, the automatic floor-disinfection robot includes a moving device 1, a disinfection device 5. The disinfection device 5 is arranged on the moving device 1. The moving device 1 includes a chassis moving mechanism 2, a support plate 3 and a top plate 4 successively arranged from bottom to top. A bottom wall of the chassis moving mechanism 2 is provided with a driving device and a wheel. The wheel is in transmission connection with the driving device. Specifically, the number of the wheel is four, and the four wheels are capable of independently steering. A control panel is arranged on the top plate 4. A battery, an electric control board and a control system are arranged inside the top plate 4. The control system is arranged on the electric control board. The control system is configured to control the automatic floor-disinfection robot to operate intelligently according to a preset program or instruction. The driving device is electrically connected to the control system. The control system is configured to control the driving device to operate, so as to drive the automatic floor-disinfection robot to move on the floor. The battery is configured to supply power to the automatic floor-disinfection robot. The battery is capable of recharging when power is almost running out, and being used again. It is similar to floor sweepers in prior art.

The disinfection device includes a disinfection assembly and a baffle 6.

The disinfection assembly is configured to perform a uniform and sufficient disinfection on the floor to be disinfected. The disinfection assembly includes a liquid supply mechanism 7, a liquid spray mechanism 8 and a fan 9. The liquid supply mechanism 7 is arranged on the moving device 1. The liquid spray mechanism 8 is arranged below the liquid supply mechanism 7. The fan 9 is arranged at a bottom center of the moving device 1.

The baffle 6 is configured to prevent the liquid spray mechanism 8 from spraying a disinfectant onto an obstacle. The baffle is arranged on a periphery of the moving device 1.

Specifically, when disinfecting the floor of a hospital room, the automatic floor-disinfection robot is started through the control panel arranged on the top plate 4. The control system arranged inside the top plate 4 controls the driving device to operate to drive the moving device 1 automatically move on the floor. During moving, the disinfection device 5 disinfects the floor. When the disinfection device 5 operates, the liquid supply mechanism 7 transfers disinfectant to the liquid spray mechanism 8. the liquid spray mechanism 8 sprays and evenly wipes the disinfectant on the floor by, contributing to a uniform spraying of the disinfectant. The fan 9 is configured to disperse the disinfectant to allow the disinfectant to be dispersed widely and uniformly. When the moving device 1 will encounter a obstacle during moving, the baffle is blocked between the liquid spray mechanism 8 and the obstacle to prevent the liquid spray mechanism 8 from spraying the disinfectant onto the obstacle, which avoids unnecessary troubles such as corrosion or contamination of obstacle.

Figure 5:
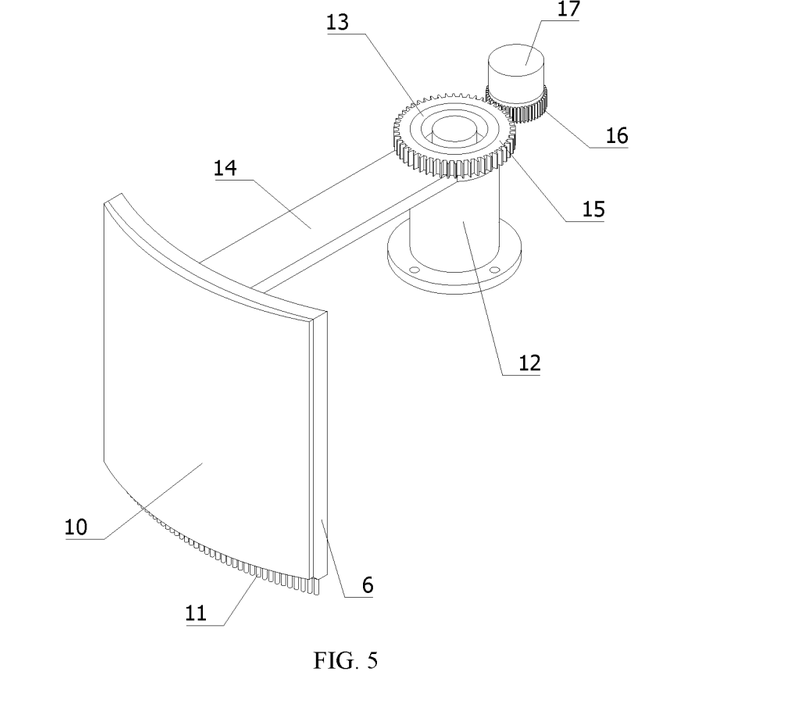
FIG. 5 is a perspective view of a baffle according to an embodiment of the present disclosure.

In order to protect the obstacle from disinfectant, a technical solution is provided below, shown as FIG. 5.

The baffle 6 has an arc-shaped structure, and is capable of rotating along the periphery of the moving device 1. The baffle 6 and the top plate 4 are arranged coaxially. A peripheral side wall of the baffle 6 is provided with a cushion 10. The cushion 10 is configured to cushion impact when touching the obstacle. A bottom of the baffle 6 is provided with a brush 11. A protection range of the baffle 6 is at least larger than a spraying range of the liquid spray mechanism 8. The brush 11 is in contact with the floor to be disinfected. The brush 11 is configured to prevent disinfectant leaking and abrasion of the bottom of the baffle.

Specifically, when the moving device 1 moves, the liquid spray mechanism 8 sprays the disinfectant on the floor. If the obstacle is observed by the automatic floor-disinfection robot, the control system controls the baffle 6 to rotate to face towards the obstacle, such that the baffle 6 shields the liquid spray mechanism 8 in a obstacle direction. When the baffle 6 touches the obstacle, the cushion 10 plays a cushioning effect, and protects the moving device 1. By means of the baffle 6, the disinfectant cannot be sprayed on the obstacle. The brush 11 prevents the disinfectant from splashing on the obstacle, and protects the baffle 6 from abrasion if the baffle 6 is always in contact with the floor.

In an embodiment, the baffle 6 is rotatable in a circumferential direction of the top plate 4. A center of the top plate 4 is fixedly connected to a center of the support plate 3 through a support column 12. An upper portion of the support column 12 is provided with a first boss. The first boss is sleeved with a sleeve 13. The sleeve 13 is pivotally connected to the first boss, such that the sleeve 13 can rotate around the first boss. An inner side of the baffle 6 is fixedly connected to the sleeve 13 through a connecting rod 14, where the inner side of the baffle 6 is arranged away from the cushion 10. A ring gear 15 is fixedly sleeved on the sleeve 13. A driving gear 16 is provided at a side of the ring gear, and is engaged with the ring gear 15. A rotating motor 17 is fixedly arranged inside the top plate 4. The rotating motor 17 is configured to drive the driving gear 16 to rotate. The rotating motor 17 is electrically connected to the control system. The rotating motor 17 can drive the driving gear 16 to rotate, and further drive the ring gear 15 and the sleeve 13 to rotate, such that the baffle 16 is driven to rotate in the circumferential direction of the top plate 4 through the connecting rod 14.

Specifically, the moving device 1 moves in other direction after spraying one part of the floor. If the automatic floor-disinfection robot meets a obstacle again, the control system controls the rotating motor 17 to drive the driving gear 16 to rotate. The sleeve 13 will rotate then since the ring gear 15 is engaged with the driving gear 16. Therefore, the baffle 6 will rotate in the circumferential direction of the top plate 4 till the baffle faces towards the obstacle. Due to the protection of the baffle 6, the obstacle will be protected from disinfectant splashing during spraying, such that the baffle 6 can resist disinfectant splashing when the moving device 1 meets the obstacle in any direction.

Figure 6:
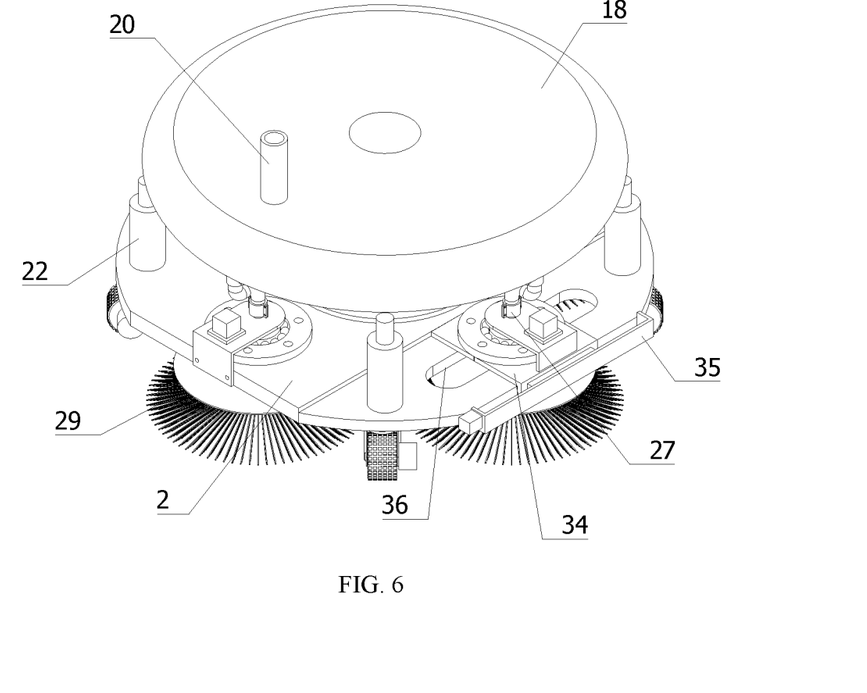
FIG. 6 is a perspective view of a disinfection assembly according to an embodiment of the present disclosure.
Figure 7:
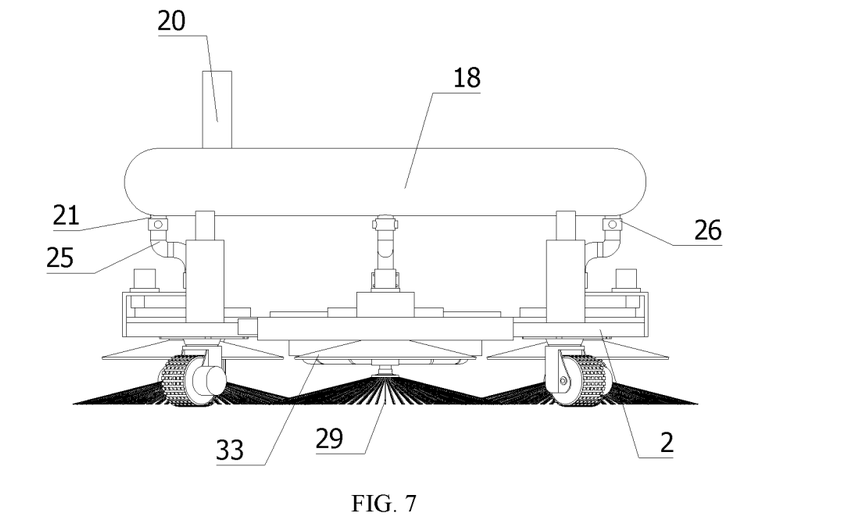
FIG. 7 is a front view of the disinfection assembly according to an embodiment of the present disclosure.

In order to ensure that the liquid spray mechanism 8 can be supplied with disinfectant, a technical solution is provided below, shown as FIGS. 6 and 7.

The liquid supply mechanism 7 includes a liquid storage vessel 18. The liquid storage vessel 18 has a flat cylindrical shape. A middle part of the liquid storage vessel 18 is provided with a connecting hole. The liquid storage vessel 18 is coaxially sleeved on the support column 12 through the connection hole. Four support bases 19 are evenly arranged at a top of the support plate 3. The liquid storage vessel 18 is arranged on the four support bases 19, or in an area between the four support bases 19. The liquid storage vessel 18 is provided with a feeding port 20. The feeding port 20 penetrates upward a top surface of the top plate, so as to facilitate liquid feeding of the liquid storage vessel 18. In addition, a cover is arranged on the feeding port 20. The cover is configured to cover the feeding port 20 when not feeding liquid. A bottom of the liquid storage vessel 18 is provided with at least one discharge port 21. The at least one discharge port is communicated with the liquid spray mechanism 8. In this embodiment, four liquid spray mechanisms 8 are evenly and circumferentially arranged at the chassis moving mechanism 2. Accordingly, the bottom of the liquid storage vessel 18 is provided with four discharge ports 21, and the four discharge ports 21 are communicated with the four liquid spray mechanisms 8 in one-to-one correspondence.

Specifically, before the liquid spray mechanism 8 spays disinfectant, the liquid storage vessel 18 is full of disinfectant. The disinfectant flows in the liquid spray mechanism through the discharge port 21 so as to be sprayed by the liquid spray mechanism 8. When the disinfectant in the liquid storage vessel 18 runs out, disinfectant can be added into the liquid storage vessel 18 through the feeding port 20, so as to ensure the liquid storage vessel 18 is full of disinfectant. In consequence, the liquid spray mechanism 8 can be filled with disinfectant in time, ensuring the liquid spray mechanism 8 can spray disinfectant.

Figure 8:
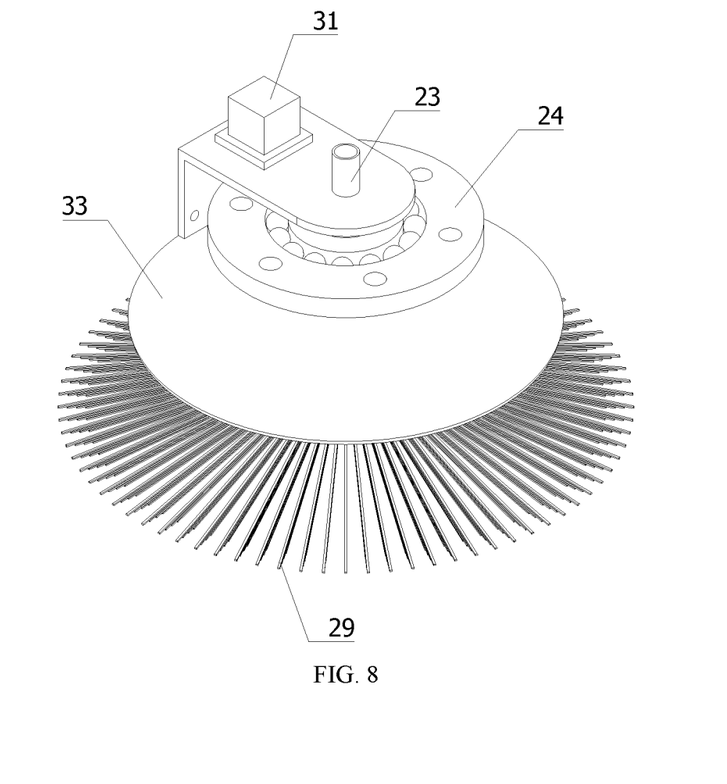
FIG. 8 is a perspective view of a liquid spray mechanism according to an embodiment of the present disclosure.
Figure 15:
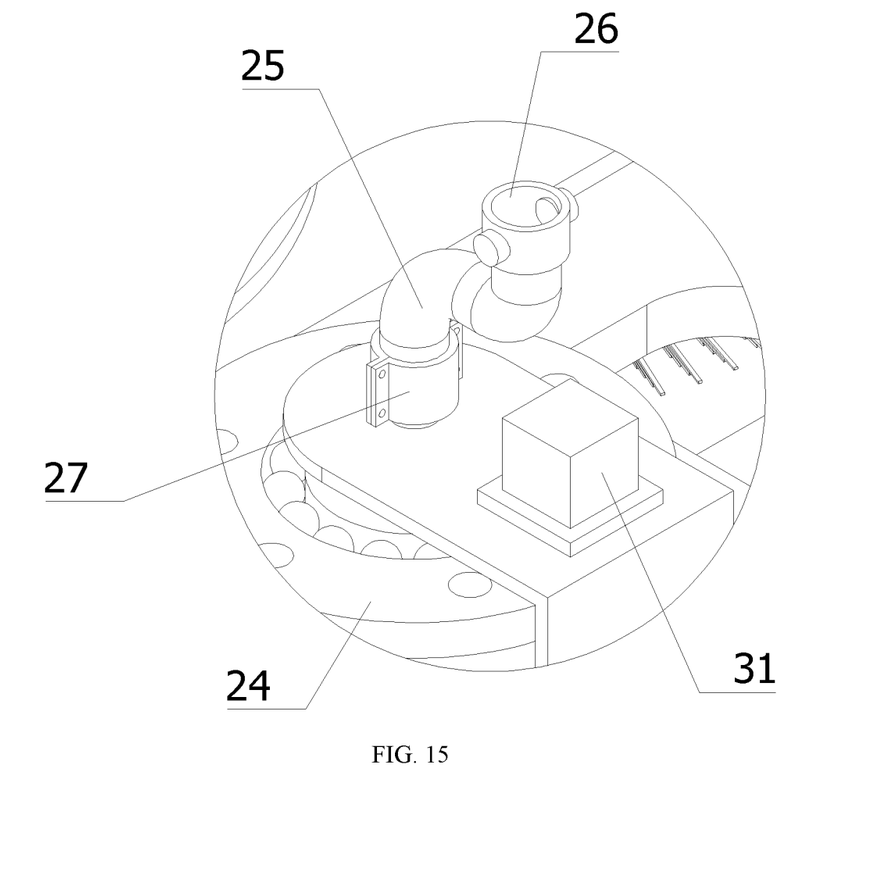
FIG. 15 is an enlarged view of part C in FIG. 13.

In order to make the liquid spray mechanism 8 to cooperate with the liquid storage vessel 18 to spray, a technical solution is provided below, shown as FIGS. 7-8 and 15.

In an embodiment, the chassis moving mechanism 2 is peripherally provided with the four liquid spray mechanisms 8. The chassis moving mechanism 2 is fixedly connected to the support plate 3 through four upright columns 22 circumferentially arranged. The four liquid spray mechanisms 8 are in one-to-one correspondence to the discharge ports 21. Each of the four liquid spray mechanisms 8 includes a spray pipe 23, a ball bearing 24, a hose 25 and a solenoid valve 26. The ball bearing 24 is provided on the chassis moving mechanism 2. An inner ring of the ball bearing 24 is fixedly sleeved on an outer circumference of the spray pipe 23. A top end of the spray pipe 23 is connected to one of the discharge ports 21 through the hose 25. The solenoid valve 26 is arranged at a connection between the discharge port 21 and the hose 25. The solenoid valve 26 is electronically connected to the control system. A locking ring 27 is arranged at a connection between the hose 25 and the spray pipe 23 for fixing.

Specifically, when the liquid storage vessel 18 needs to be supplied with disinfectant, the solenoid valve 26 of each hose 25 is opened, such that disinfectant in the liquid storage vessel 18 can flow out from the discharge port 21 and enter into the hose 25. The disinfectant further flows through the hose 25 and enters into the spray pipe 23, such that the disinfectant can be sprayed from the spray pipe 23 onto the floor. After the disinfection is completed, the solenoid valve 26 is closed to avoid too much disinfectant spraying. Upon the solenoid valve 26 is closed, the disinfectant in the liquid storage vessel stops outputting, such that the spray pipe 23 cannot spray disinfectant.

Figure 9:
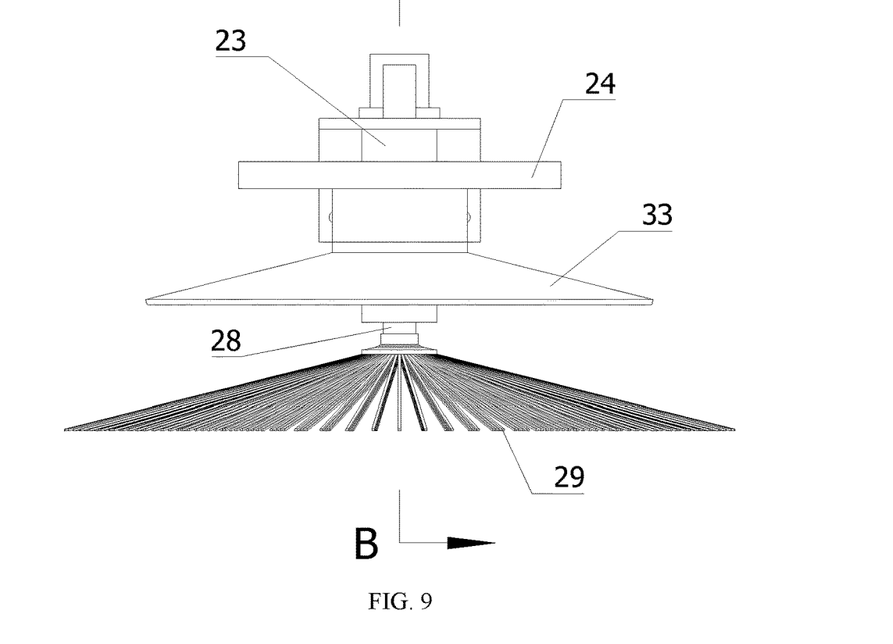
FIG. 9 is a side view of the liquid spray mechanism according to an embodiment of the present disclosure.
Figure 10:
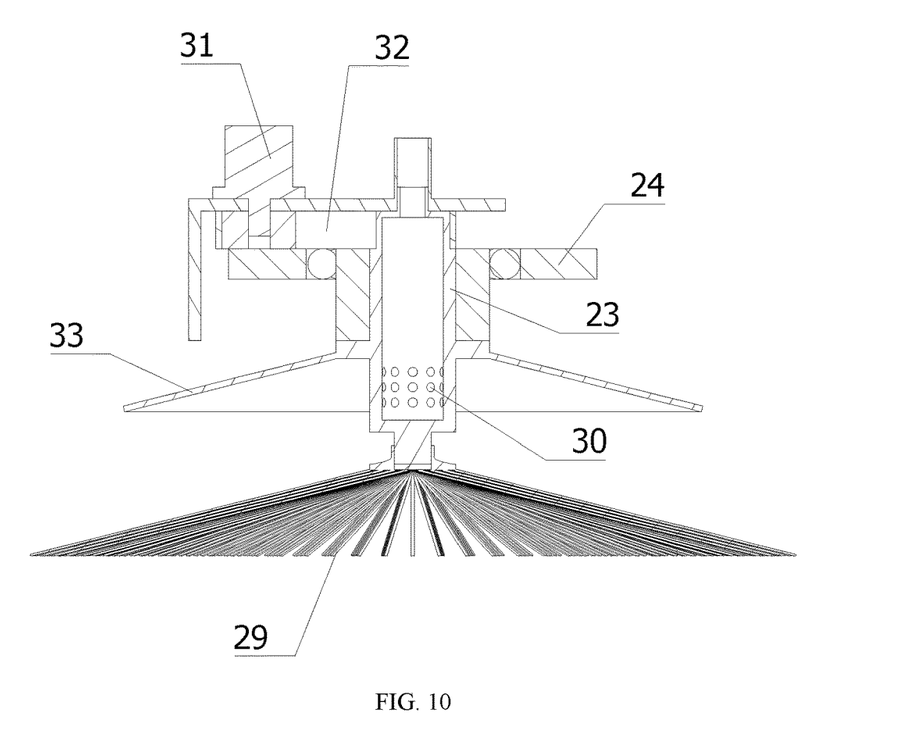
FIG. 10 is a sectional view of the liquid spray mechanism along B-B line in FIG. 9.

In order to make the disinfectant being uniformly sprayed on the floor through the spray pipe 23, a technical solution is provided below, shown as FIGS. 8-10.

A bottom end of the spray pipe 23 is provided with a second boss 28. Four sweeping brushes 29 are fixedly connected to the second boss 28, and are configured to disinfect the floor in a sweep-manner. A brush end of each of the sweeping brush 29 is always in contact with the floor. The four sweeping brushes 29 are evenly arranged around the fan 29.

Specifically, when the spray pipe 23 sprays the disinfectant, the disinfectant in the spray pipe 23 flows to the sweeping brush 29, such that the disinfectant can be uniformly wiped on the floor by the sweeping brushes 29. In order to achieve a wider and more even disinfectant dispersion, the fan 9 can blow away the disinfectant on the floor to avoid an accumulation of the disinfectant. The accumulation of the disinfectant not only waste disinfectant, but also make a poorer floor disinfection effect. Moreover, the fan 9 can effectively blow the disinfectant attached to the sweeping brush 29 to the floor. During operation of the fan 9, a bottom surface of the fan 9 and the floor form an air cavity. The air blown by the fan 9 will be blown to the sweeping brushes 29 due to the obstruction of the floor, such that the disinfectant can be efficiently and uniformly sprayed on the floor.

In order to make the disinfectant being sprayed to the sweeping brushes 29, a technical solution is provided below, shown as FIG. 10.

A circumferential wall of a lower portion of the spray pipe 23 is evenly provided with multiple spray ports 30. The chassis moving mechanism 2 is provided with a frame corresponding to the spray pipe 23. A driving motor 31 is arranged on the frame to drive the spray pipe 23 to rotate. The driving motor 31 is electrically connected to the control system. An output end of the driving motor 31 is connected to an upper portion of the spray pipe 23 through a synchronous belt 32. The driving motor 31 is configured to drive the spray pipe 23 to rotate around the ball bearing 24.

Specifically, when the disinfectant is introduced into the spray pipe 23, the driving motor 31 drives the spray pipe 23 to rotate on the ball bearing 24. An inner ring of the ball bearing 24 rotates, and an outer ring of the ball bearing 24 is fixed. Since the spray pipe 23 is provided with the spray ports 30, the disinfectant in the spray pipe 23 will be thrown out from the spray ports 30 when the spray pipe 23 rotates, and then fell on the sweeping brushes 29. The sweeping brushes 29 attached with the disinfectant can sweep the floor to disinfect, which ensures that the disinfectant can be uniformly dispersed when disinfecting, improving the effectiveness of disinfection.

In order to prevent the disinfectant from being sprayed on the obstacles when the disinfectant sprays from the spray pipe 23, a technical solution is provided below, shown as FIGS. 8-10.

A covering plate 33 is sleevedly provided on the spray pipe 23. An umbrella-shaped opening is arranged in the covering plate 33 to cover the lower portion of the spray pipe 23. The spray pipe 23 is centrally located below the covering plate 33.

Specifically, when the spray pipe 23 sprays the disinfectant, the covering plate 33 enables the disinfectant to splash downward. Consequently, the sweeping brushes 29 are splashed with the disinfectant, and the obstacles is protected from being sprayed with disinfectant. The sweeping brushes 29 with the disinfectant can sweep the floor to disinfect. Moreover, the fan 9 can blow the disinfectant to render the disinfectant being sprayed uniformly, making a better disinfection effect.

Figure 13:
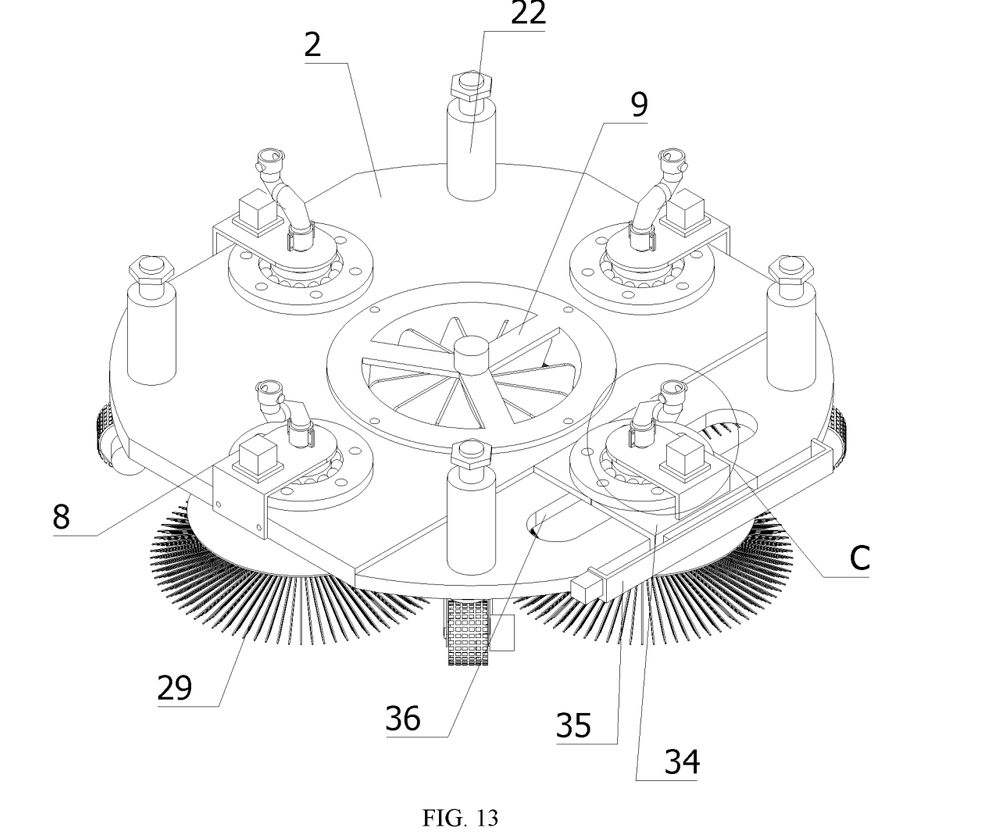
FIG. 13 is a perspective view of combination of a chassis moving mechanism and the liquid spray mechanism according to an embodiment of the present disclosure.
Figure 14:
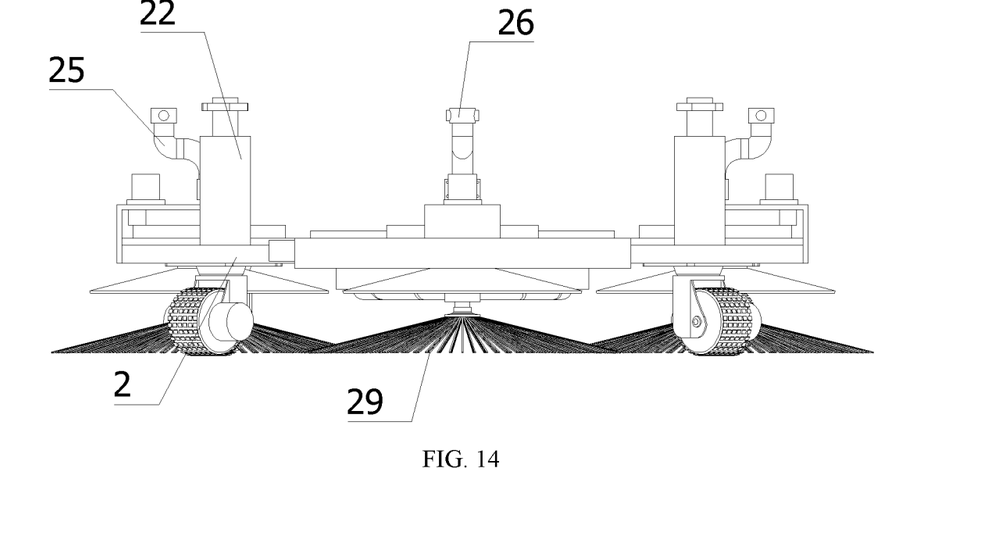
FIG. 14 is a front view of the combination of the chassis moving mechanism and the liquid spray mechanism according to an embodiment of the present disclosure.

In order to disinfect the floor at corner when the moving device 1 moves to the corner, a technical solution is provided below, shown as FIGS. 13-14.

The four liquid spray mechanisms 8 consist of a first liquid spray mechanism, a second liquid spray mechanism, a third liquid spray mechanism and a fourth liquid spray mechanism. The first liquid spray mechanism is capable of moving horizontally. A periphery of the chassis moving mechanism 2 is formed by straight edges. The first liquid spray mechanism capable of moving horizontally is arranged on a sliding plate 34. An edge of the chassis moving mechanism 2 corresponding to the first liquid spray mechanism is provided with a linear actuator 35. The linear actuator 35 is configured to drive the sliding plate 34 to move horizontally along the edge corresponding to the first liquid spray mechanism. The chassis moving mechanism 2 is further provided with an elongated hole 36, and the elongated hole 36 does not hinder horizontal motion of the first liquid spray mechanism.

The linear actuator 35 includes a rectangular frame and a threaded shaft. The rectangular frame is connected to a side wall of the chassis moving mechanism 2. The threaded shaft is penetratedly arranged in the rectangular frame. Two ends of the threaded shaft are pivotally connected to two side walls of the rectangular frame. An outer side wall of the rectangular frame is provided with a micro motor. An output shaft of the micro motor is fixedly connected to the threaded shaft. The micro motor is electrically connected to the control system. The micro motor is configured to drive the threaded shaft to rotate. An outer side of the sliding plate 34 is fixedly connected to a thread bushing. The thread bushing is embedded in the rectangular frame. The threaded shaft is penetratedly arranged in the thread bushing, and is and threadedly connected to the thread bushing. The threaded shaft is configured to rotate to drive the sliding plate 34 and the liquid spray mechanism 8 arranged on the sliding plate 34 to move laterally along the elongated hole 36.

Specifically, when the moving device 1 moves to a corner, the linear actuator 35 drives the sliding plate 34 to move along the straight edge of the chassis moving mechanism 2, such that the liquid spray mechanism 8 on the sliding plate 34 moves towards the corner. In consequence, the sweeping brush 29 on the liquid spray mechanism 8 can brush the disinfectant to the floor in the corner.

Figure 1:
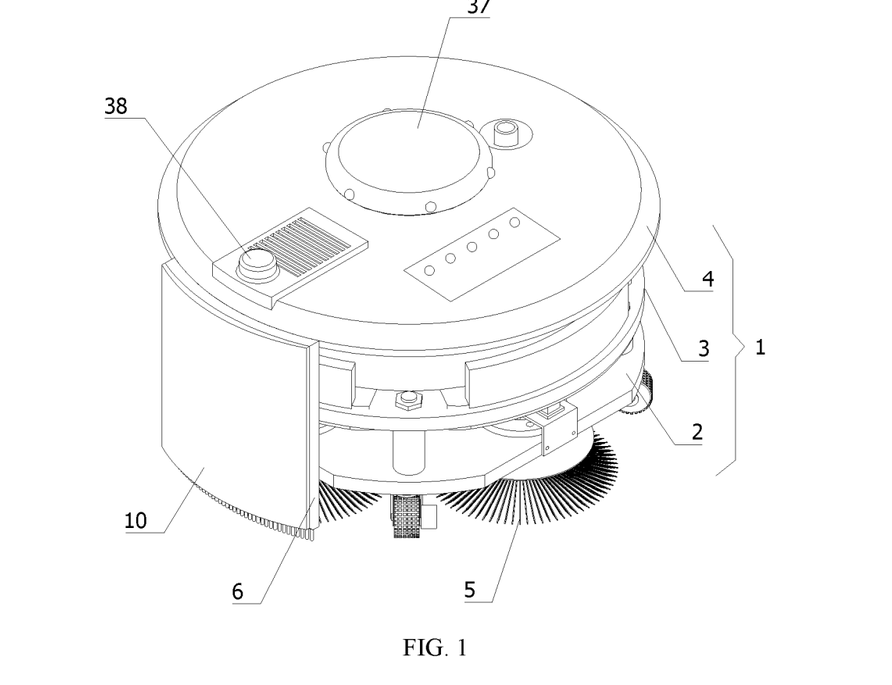
FIG. 1 is a perspective view of an automatic floor-disinfection robot according to an embodiment of the present disclosure.
Figure 2:
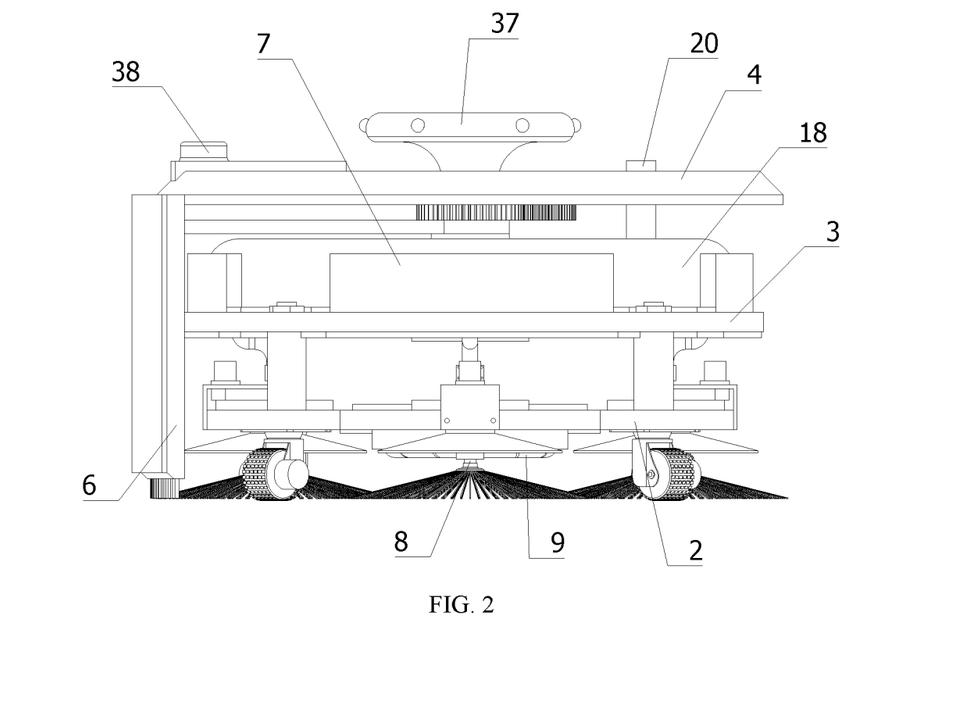
FIG. 2 is a front view of the automatic floor-disinfection robot according to an embodiment of the present disclosure.
Figure 3:
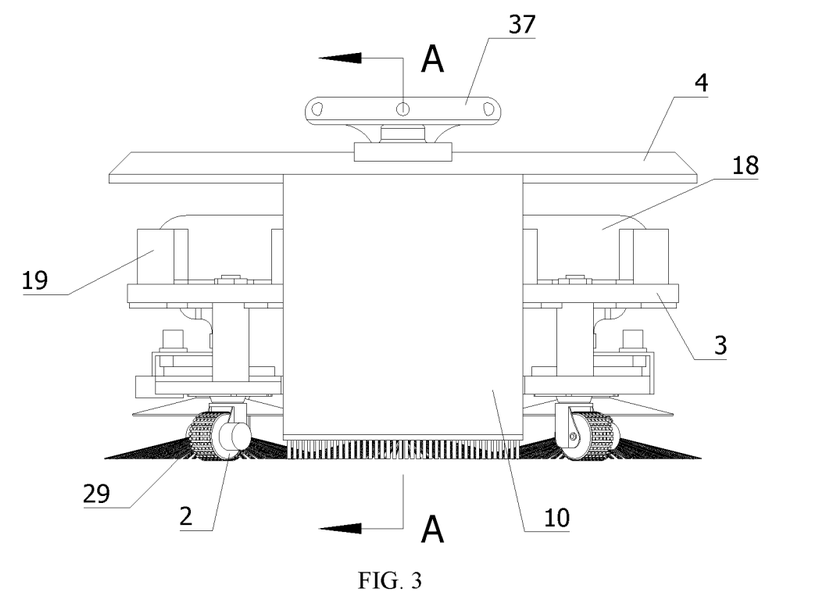
FIG. 3 is a side view of the automatic floor-disinfection robot according to an embodiment of the present disclosure.
Figure 4:
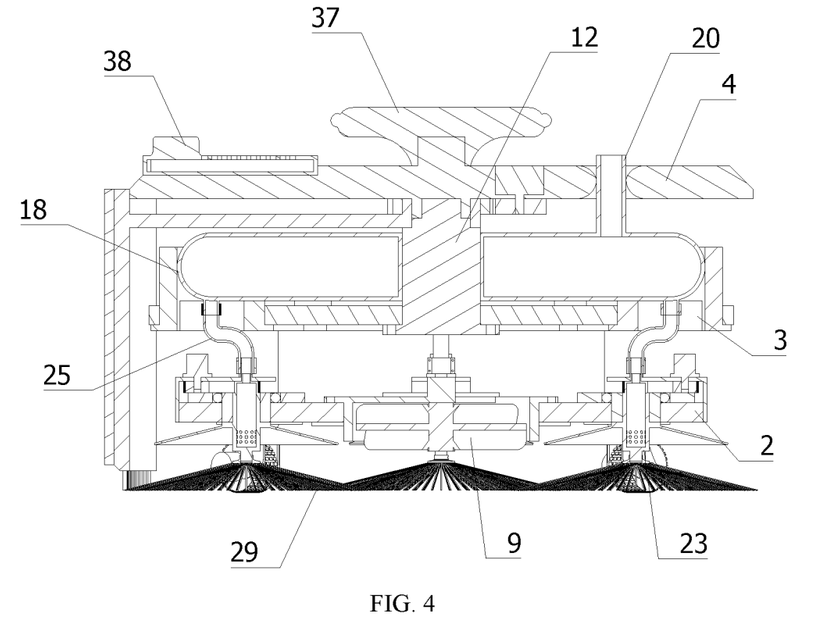
FIG. 4 is a sectional view of the automatic floor-disinfection robot along A-A line in FIG. 3.
Figure 11:
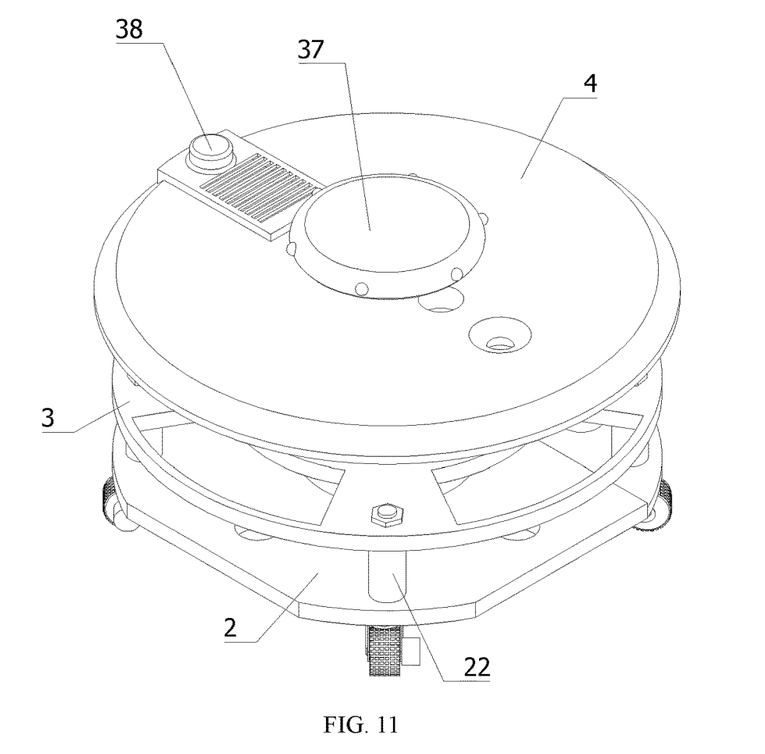
FIG. 11 is a perspective view of a moving device according to an embodiment of the present disclosure.
Figure 12:
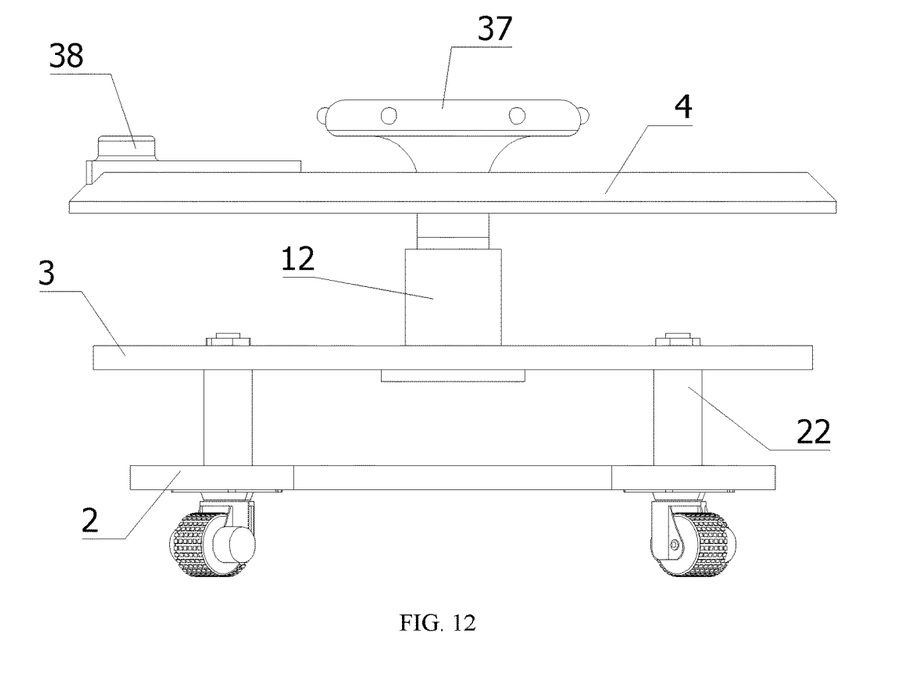
FIG. 12 is a front view of the moving device according to an embodiment of the present disclosure.

In order to render the moving device 1 sensing a obstacle during moving, a technical solution is provided below, shown as FIGS. 1, 11 and 12.

The automatic floor-disinfection robot further includes an omnidirectional camera 37 and an alarm 38. The omnidirectional camera 37 and the alarm 38 are arranged above the top plate 4. The omnidirectional camera 37 and the alarm 38 are electrically connected to the control system.

Specifically, when the moving device 1 moves, the omnidirectional camera 37 can observe the surrounding to prevent the moving device 1 from hitting the obstacles. When the omnidirectional camera 37 observes an approach of a people, the alarm 38 will alarm to remind the people to be careful, so as to prevent the people from stepping on the moving device 1.

Through the integration of the moving device 1 and the disinfection device 5, the automatic floor-disinfection robot provided herein can sufficiently disinfect the floor of hospital rooms. The baffle 6 shields the obstacles to protect the obstacles from being splashed with the disinfectant, ensuring that the disinfectant can only disinfect the floor. By means of the liquid spray mechanisms 8 and the fan 9, the disinfectant is uniformly spread, and the floor can be sufficiently disinfected. Through the cooperation of the omnidirectional camera 37 and the alarm 38, the moving device 1 not only comprehensively disinfects the floor, but protects the people's safety. Regarding the automatic floor-disinfection robot provided herein, a comprehensive disinfection of floor can be achieve, and the obstacles are protected from being splashed of disinfectant.

The basic principles, main features and advantages of the present disclosure are described above with reference to the embodiments. Although the disclosure have been illustrated and described in detail above, it should be understood that those skilled in the art could still make modifications and improvements to the embodiments of the disclosure. Those modifications and improvements made by those skilled in the art based on the content disclosed herein without departing from the scope of the disclosure shall fall within the scope of the present disclosure defined by the appended claims.

What is claimed is:

1. An automatic floor-disinfection robot for hospital rooms, comprising:
a moving device; and
a disinfection device;
wherein the disinfection device is arranged on the moving device;
the moving device comprises a chassis moving mechanism, a support plate and a top plate arranged successively from bottom to top; a bottom wall of the chassis moving mechanism is provided with a driving device and a wheel; the wheel is in transmission connection with the driving device; a control panel is arranged on the top plate; a battery, an electric control board and a control system are arranged inside the top plate; and the control system is arranged on the electric control board;
the disinfection device comprises a disinfection assembly and a baffle;
the disinfection assembly comprises a liquid supply mechanism, four liquid spray mechanisms and a fan; the liquid supply mechanism is arranged on the moving device; the four liquid spray mechanisms are arranged below the liquid supply mechanism; and the fan is arranged at a bottom center of the moving device;
the baffle is configured to prevent the four liquid spray mechanisms from spraying a disinfectant onto an obstacle; the baffle is arranged on a periphery of the moving device; the baffle has an arc-shaped structure, and is rotatable along the periphery of the moving device; the baffle and the top plate are arranged coaxially; the top plate is connected to the support plate through a support column; the support column is provided with a first boss; a sleeve is pivotally connected to the first boss; the baffle is fixedly connected to the sleeve through a connecting rod; a ring gear is fixedly sleeved on the sleeve; a driving gear is provided at a side of the ring gear, and is engaged with the ring gear; a rotating motor is fixedly arranged inside the top plate; the rotating motor is configured to drive the driving gear to rotate; and the rotating motor is electrically connected to the control system; and
the four liquid spray mechanisms are evenly and circumferentially arranged at the chassis moving mechanism; the four liquid spray mechanisms consist of a first liquid spray mechanism, a second liquid spray mechanism, a third liquid spray mechanism and a fourth liquid spray mechanism; the first liquid spray mechanism is capable of moving horizontally; a periphery of the chassis moving mechanism is formed by straight edges; the first liquid spray mechanism is arranged on a sliding plate; an edge of the chassis moving mechanism corresponding to the first liquid spray mechanism is provided with a linear actuator; the linear actuator is configured to drive the sliding plate to move horizontally along the edge corresponding to the first liquid spray mechanism; the chassis moving mechanism is further provided with an elongated hole; and the elongated hole does not hinder horizontal motion of the first liquid spray mechanism.

2. The automatic floor-disinfection robot of claim 1, wherein a peripheral side wall of the baffle is provided with a cushion; a bottom of the baffle is provided with a brush; and the brush is in contact with a floor to be disinfected; and the automatic floor-disinfection robot further comprises an omnidirectional camera and an alarm; the omnidirectional camera and the alarm are arranged above the top plate; and the omnidirectional camera and the alarm are electrically connected to the control system.

3. The automatic floor-disinfection robot of claim 1, wherein the liquid supply mechanism comprises a liquid storage vessel; a middle part of the liquid storage vessel is provided with a connecting hole; the liquid storage vessel is sleeved on the support column through the connection hole; the liquid storage vessel is also provided with a feeding port; a top of the feeding port penetrates upward a top surface of the top plate; a cover is arranged on the feeding port; a bottom of the liquid storage vessel is provided with at least one discharge port; and the at least one discharge port is communicated with the four liquid spray mechanisms.

4. The automatic floor-disinfection robot of claim 3, wherein the number of the at least one discharge port is four; four discharge ports are communicated with the four liquid spray mechanisms in one-to-one correspondence; and the chassis moving mechanism is fixedly connected to the support plate through four upright columns.

5. The automatic floor-disinfection robot of claim 3, wherein each of the four liquid spray mechanisms comprises a spray pipe, a ball bearing, a hose and a solenoid valve; the ball bearing is provided on the chassis moving mechanism; an inner ring of the ball bearing is fixedly sleeved on an outer circumference of the spray pipe; a top end of the spray pipe is connected to the discharge port through the hose; the solenoid valve is arranged at a connection between the discharge port and the hose; the solenoid valve is electrically connected to the control system; and a locking ring is arranged at a connection between the hose and the spray pipe for fixing.

6. The automatic floor-disinfection robot of claim 5, wherein a bottom end of the spray pipe is provided with a second boss; four sweeping brushes are fixedly connected to the second boss; a brush end of each of the four sweeping brush is in contact with a floor to be disinfected; and the four sweeping brushes are evenly arranged around the fan.

7. The automatic floor-disinfection robot of claim 5, wherein a circumferential wall of a lower portion of the spray pipe is provided with a plurality of spray ports; the chassis moving mechanism is provided with a frame corresponding to the spray pipe; a driving motor is arranged on the frame; the driving motor is electrically connected to the control system; an output end of the driving motor is connected to an upper portion of the spray pipe through a synchronous belt; and the driving motor is configured to drive the spray pipe to rotate around the ball bearing.

8. The automatic floor-disinfection robot of claim 5, wherein a covering plate is sleevedly provided on the spray pipe; an umbrella-shaped opening is arranged in the covering plate to cover a lower portion of the spray pipe; and the spray pipe is centrally located below the covering plate.

9. The automatic floor-disinfection robot of claim 1, wherein the linear actuator comprises a rectangular frame and a threaded shaft; the rectangular frame is connected to a side wall of the chassis moving mechanism; the threaded shaft is penetratedly arranged in the rectangular frame; two ends of the threaded shaft are pivotally connected to two side walls of the rectangular frame, respectively; an outer side wall of the rectangular frame is provided with a micro motor; an output shaft of the micro motor is fixedly connected to the threaded shaft; the micro motor is electrically connected to the control system; the micro motor is configured to drive the threaded shaft to rotate; an outer side of the sliding plate is fixedly connected to a thread bushing; the thread bushing is embedded in the rectangular frame; the threaded shaft is penetratedly arranged in the thread bushing, and is threadedly connected to the thread bushing; and the threaded shaft is configured to rotate to drive the sliding plate and the liquid spray mechanism arranged on the sliding plate to move laterally along the elongated hole.

\* \* \* \* \*